US010579866B2

(12) United States Patent
Bedrosian et al.

(10) Patent No.: US 10,579,866 B2
(45) Date of Patent: Mar. 3, 2020

(54) METHOD AND SYSTEM FOR ENHANCING USER ENGAGEMENT DURING WELLNESS PROGRAM INTERACTION

(71) Applicant: Johnson & Johnson Health and Wellness Solutions, Inc., Ann Arbor, MI (US)

(72) Inventors: Richard C. Bedrosian, Shrewsbury, MA (US); Amy Michelle Bucher, Boston, MA (US); Keith Carlson, Ann Arbor, MI (US); Maurice Collins, Chelsea, MI (US); Shawn Thomas Mason, Ann Arbor, MI (US); Jeffrey Matthes, Ypsilanti, MI (US); Janeta Nikolovski, Princeton, NJ (US); Raphaela Finkenauer O'Day, Wildwood, MO (US); Caren Phipps, Howell, NJ (US); Thomas E. Sox, Ambler, PA (US); Thomas Matthew Walsh, Tecumseh, MI (US)

(73) Assignee: Johnson & Johnson Health and Wellness Solutions, Inc., Ann Arbor, MI (US)

( * ) Notice: Subject to any disclaimer, the term of this patent is extended or adjusted under 35 U.S.C. 154(b) by 237 days.

(21) Appl. No.: 15/259,453

(22) Filed: Sep. 8, 2016

(65) Prior Publication Data
US 2017/0053157 A1    Feb. 23, 2017

Related U.S. Application Data

(62) Division of application No. 14/074,129, filed on Nov. 7, 2013, now abandoned.

(Continued)

(51) Int. Cl.
*A61B 5/16* (2006.01)
*A61B 5/01* (2006.01)
(Continued)

(52) U.S. Cl.
CPC ............ *G06K 9/00302* (2013.01); *A61B 5/01* (2013.01); *A61B 5/021* (2013.01); *A61B 5/024* (2013.01);
(Continued)

(58) Field of Classification Search
CPC ........... A61B 5/16; A61B 5/165; A61B 5/167; A61B 5/68
(Continued)

(56) References Cited

U.S. PATENT DOCUMENTS 5,937,387 A    8/1999    Summerell
5,949,785 A    9/1999    Beasley
(Continued)

OTHER PUBLICATIONS

J.A.Gazmararian, et al., "Comparing the Predictive Accuracy of health Risk Appraisal: the Centers for Disease Control Versus Carter Center Program", American Journal of Public Health, 81 :1296-1301 (1991).

(Continued)

*Primary Examiner* — Christopher A Flory (57) ABSTRACT

A method and system for enhancing user engagement during wellness program interaction includes presenting health information to the user, collecting data and modifying the information presented to the user in enhance the user's engagement with the wellness program.

18 Claims, 8 Drawing Sheets

Related U.S. Application Data (60) Provisional application No. 61/727,337, filed on Nov. 16, 2012.

(51) Int. Cl.
  *A61B 5/021* (2006.01)
  *A61B 5/024* (2006.01)
  *A61B 5/11* (2006.01)
  *A61B 5/00* (2006.01)
  *G06K 9/00* (2006.01)

(52) U.S. Cl.
  CPC .............. *A61B 5/11* (2013.01); *A61B 5/165* (2013.01); *A61B 5/441* (2013.01); *G06K 9/00255* (2013.01)

(58) Field of Classification Search
  USPC .......................... 600/301, 300; 482/8; 705/2
  See application file for complete search history.

(56) References Cited

U.S. PATENT DOCUMENTS

| | | |
|---|---|---|
| 5,997,439 A | 12/1999 | Ohsuga |
| 6,032,156 A | 2/2000 | Marcus |
| 6,159,131 A | 12/2000 | Pfeffer |
| 6,208,974 B1 | 3/2001 | Campbell |
| 6,241,641 B1 | 6/2001 | Sawyer |
| 6,244,987 B1 | 6/2001 | Ohsuga |
| 6,269,339 B1 | 7/2001 | Silver |
| 6,705,972 B1 | 3/2004 | Takano |
| 7,225,414 B1 | 5/2007 | Sharma |
| 7,319,779 B1 | 1/2008 | Mummareddy |
| 7,412,511 B2 | 8/2008 | Curry |
| 7,505,621 B1 | 3/2009 | Agrawal |
| 7,583,253 B2 | 9/2009 | Jeng et al. |
| 7,586,418 B2 | 9/2009 | Cuddihy |
| 7,654,949 B2 | 2/2010 | McNew |
| 7,698,238 B2 | 4/2010 | Barletta et al. |
| 7,756,744 B2 | 7/2010 | Schiff et al. |
| 7,764,311 B2 | 7/2010 | Bill |
| 7,772,965 B2 | 8/2010 | Farhan |
| 7,895,078 B2 | 2/2011 | Schiff et al. |
| 7,904,477 B2 | 3/2011 | Jung |
| 7,925,519 B2 * | 4/2011 | Greene ................ G06F 19/328 705/2 |
| 7,949,712 B2 | 5/2011 | Friedman |
| 7,967,731 B2 | 6/2011 | Kil |
| 8,027,822 B2 | 9/2011 | Turgiss |
| 8,083,675 B2 | 12/2011 | Robinson et al. |
| 8,109,874 B2 | 2/2012 | Kong et al. |
| 8,112,293 B2 | 2/2012 | Howell |
| 8,125,314 B2 | 2/2012 | Fithian et al. |
| 8,219,438 B1 | 7/2012 | Moon et al. |
| 8,271,865 B1 | 9/2012 | Bennett |
| 8,321,006 B1 | 11/2012 | Snyder |
| 8,346,524 B2 | 1/2013 | Turgiss |
| 8,348,809 B2 | 1/2013 | van der Zande |
| 8,388,532 B2 | 3/2013 | Morgan |
| 8,457,466 B1 | 6/2013 | Sharma |
| 8,462,927 B2 | 6/2013 | Gehm |
| 8,489,539 B2 | 7/2013 | DiCanio |
| 8,527,213 B2 | 9/2013 | Kailas |
| 2004/0117212 A1 | 6/2004 | Kong |
| 2005/0223237 A1 | 10/2005 | Barletta |
| 2006/0143647 A1 | 6/2006 | Bill |
| 2008/0201174 A1 * | 8/2008 | Ramasubramanian ...................... G06F 19/3456 705/3 |
| 2009/0118588 A1 | 5/2009 | Robinson |
| 2009/0156982 A1 | 6/2009 | Petrie |
| 2010/0125507 A1 | 5/2010 | Tarantino, III |
| 2010/0331146 A1 | 12/2010 | Kil |
| 2011/0022332 A1 | 1/2011 | Kailas |
| 2011/0112881 A1 | 5/2011 | Malhotra et al. |
| 2011/0169603 A1 | 7/2011 | Fithian |
| 2011/0238604 A1 | 9/2011 | DiCanio |
| 2012/0036015 A1 | 2/2012 | Sheikh |
| 2012/0116797 A1 | 5/2012 | Strecher et al. |
| 2012/0278414 A1 | 11/2012 | Walsh et al. |
| 2012/0290950 A1 | 11/2012 | Rapaport |
| 2013/0187768 A1 | 7/2013 | Eisterhold |
| 2014/0032234 A1 * | 1/2014 | Anderson .............. G06Q 50/22 705/2 |
| 2014/0100867 A1 * | 4/2014 | York ..................... G06Q 50/22 705/2 |
| 2014/0114680 A1 * | 4/2014 | Mills ..................... G16H 50/30 705/2 |
| 2014/0142967 A1 | 5/2014 | Bedrosian |
| 2014/0344718 A1 | 11/2014 | Rapaport |

OTHER PUBLICATIONS

Ekman et al., "Constants across cultures in the face and emotion", Journal of Personality and Social Psychology, 17(2):124-129 (1971).

Devries, George Thomas III, "Innovations in Workplace Wellness: Six New Tools to Enhance Programs and Maximize Employee Health and Productivity", Compensation & Benefits Review 42:46 (2010).

Ducheneaut et al., "Body and Mind, a Study of Avatar Personalization in Three Virtual Worlds", Proc. of CHI 2009).

Christine Blackman, "Your Avatar can Influence Real World Behavior", Stanford Report (Feb. 25, 2010).

Christine Puder, "The Healthful Effects of Laughter", The International Child and Youth Care Network, Issue 55 (Aug. 2003).

\* cited by examiner

Determination of User Engagement Level and Modification of Content Based on User Engagement

METHOD AND SYSTEM FOR ENHANCING USER ENGAGEMENT DURING WELLNESS PROGRAM INTERACTION

CROSS-REFERENCE TO RELATED APPLICATION

This application is a division of U.S. application Ser. No. 14/074,129, filed Nov. 7, 2013 and claims benefit of U.S. Provisional Application 61/727,337, filed Nov. 16, 2012. The complete disclosure of the aforementioned related U.S. patent applications are hereby incorporated herein by reference for all purposes.

FIELD OF THE INVENTION

The present invention relates to a method and system for enhancing user engagement during wellness program interaction.

BACKGROUND OF THE INVENTION

Health Risk Assessment

The health risk assessment (or HRA) is a commonly used tool for determining the health risk factors of an individual, as well as predicting future morbidity and mortality of the individual. The HRA was originally intended to determine the factors that predicted the life expectancy of an individual. This type of assessment has been in use for at least 30 years, and its predictive potential was based on various long-term epidemiological studies involving large numbers of subjects. These studies assessed health status parameters with survey questions as well as direct physiological measurements. The data collected from the subjects were compared with development of disease and the eventual death of these individuals. This analysis provided information correlating specific behavioral and physiological factors with disease development and lifespan. A comprehensive discussion of this type of HRA is provided in "Comparing the Predictive Accuracy of Health Risk Appraisal: The Centers for Disease Control Versus Carter Center Program" (J. A. Gazmararian, et al., American Journal of Public Health, 81:1296-1301 (1991)), which in incorporated herein by reference.

Subsequent development of HRAs moved beyond the primarily passive nature of earlier HRAs, and incorporated queries to determine the desire of the individual to change potentially detrimental behaviors, the degree of readiness of the individual to make the indicated changes, and the strength of the belief that the individual could make successful behavior changes. Research on more effective health promotion and the advent of more economical digital processing facilitated these improvements to HRAs.

Workplace Wellness

Workplace wellness is any workplace health promotion activity or organizational policy designed to support healthy behavior in the workplace and to improve health outcomes. Generally speaking, health promotion is defined as "the process of enabling people to increase control over, and to improve their health," (World Health Organization. Health Promotion Glossary. http://www.who.int/hpr/NPH/docs/hp-_glossary_en.pd) and health promotion can be carried out in the workplace as well as in many other settings. Workplace wellness has been expanded over the past decade to encompass the overall creation of a "culture of health" within the worksite. DeVries, George Thomas III. Innovations in Workplace Wellness: Six New Tools to Enhance Programs and Maximize Employee Health and Productivity. Compensation & Benefits Review (2010) 42:46. Workplace wellness programs consist of a variety of activities such as health fairs, health education, medical screenings, health coaching, weight management programs, wellness newsletters, on-site fitness programs and/or facilities and educational programs. These programs address a broad range of objectives, including smoking cessation, stress management, and weight loss.

Informational and educational strategies attempt to build the knowledge base necessary to inform optimal health practices. Information and learning experiences facilitate voluntary adaptations of behavior conducive to health. Examples include health-related information provided on the company intranet, nutrition education software, and information about the benefits of healthy diet and exercise. Behavioral and social strategies attempt to influence behaviors indirectly by targeting individual cognition (awareness, self-efficacy, perceived support, intention) believed to mediate behavior changes.

Low participation rates by employees significantly limit the potential benefits of wellness programs. Little is known or reported about the determinants of participation, but some clues are emerging. Ongoing management support and accountability are critical to successful worksite health promotion programs. One reason for low participation rates may have to do with the messaging associated with the policy or program. In order to motivate or persuade employees to participate and change behavior, messages should be individually targeted which results in more significant positive attitude change.

Message Delivery

Different methods and/or systems for the delivery of information to individuals are known. For example, U.S. Pat. No. 7,949,712 to AT&T Intellectual Property L.L.P., discloses a method for deploying a high availability presence engine for instant messaging that includes: receiving a user's presence change information in a global table; updating the global table to reflect the change in the user's presence information; and sending updated presence information on the user to local tables of contacts affected by the change in the user's presence; and U.S. Pat. Nos. 7,756,744 and 7,895,078 to Dotomi Inc. disclose a method for messaging over a data network, comprising: i) providing an Administration Server (AS) in which user portfolios are stored, said AS being in communication with a terminal belonging to a user; ii) allowing every registered user to generate and update one or more user portfolio(s) containing information relative to Providers and/or individuals the messages of which the user is willing to view; and iii) displaying to one or more users on their terminal messages according to the information contained in the user portfolio. While many of these methods and/or systems provide information to the user, they lack the intuitiveness to decide when the message will be most effective, based on learned patterns, user feedback, lack of user feedback and user preferences as well as what the content of the message should be.

Relevancy of Messages

Methods and/or systems to determine relevancy of messages are known. U.S. Published Application No. 20120036015 to Sheikh discloses a method to improve the relevancy of rendered advertising material to one or more consumers based on user-defined preferences, geolocation, and user-granted permission.

U.S. Published Application No. 20110112881 to Malhotra et al. discloses a system and method for helping users perform and manage actions on their to-do lists of tasks by making it fun, rewarding and engaging. Malhotra et al. discloses that the system and method facilitate the interaction of a user with to-do list task items with those who can influence the user to take action and those that stand to benefit from the performance of the to-do list task items.

User Interest

Methods and/or systems for determining and/or keeping user interest are known. U.S. Pat. No. 8,125,314 to IBM discloses a method and system for determining user interest in media. The patent discloses that the method and system distinguish between user physical exertion biometric feedback and user emotional interest in a media stream.

U.S. Pat. No. 8,109,874 to Samsung Electronics Co., Ltd. discloses a mobile device capable of performing biomedical signal measurement and a health care method using the same. The patent discloses that the mobile device comprises a biomedical signal measurement module for detecting biomedical signals from a user's body, classifying the detected biomedical signals by respective signals and outputting the classified signals; and a health care module for analyzing a user's emotional state and physical condition based on the biomedical signals input from the biomedical signal measurement module and user's physical information.

U.S. Pat. No. 8,219,438 to VideoMining Corporation discloses a method and system to measure the level of shoppers' interest and their mental responses. The method and system utilize at least one overhead camera to track a shopper's movement and recognize her/his gross-level interest. The method and system also utilize at least one camera to capture the shopper's face so that the system can measure gaze and facial expressions.

U.S. Pat. No. 7,764,311 to AOL Inc. discloses a method and system that manages digital content accessed by a user. In accordance with the method and system, an image of the user is captured and analyzed to determine an actual mood of the user; a desired mood state is identified and compared to the actual mood; and content is selected based on the results of the comparison.

U.S. Pat. No. 7,698,238 to Sony Deutschland GmbH discloses an emotion control system and method for processing multimedia data. The system comprises a multimedia system for presenting multimedia content to a user, an emotion model means for determining the emotional state of the user during the presentation of the multimedia content and an editing unit for changing the multimedia content in accordance with the emotional state of the user. The emotion model means comprises an acquisition system, which detects and measures physiological reactions of the user, a processing means, which processes and evaluates the data submitted by the acquisition system, and a transformation means, which comprises algorithms for effectuating detection of an emotional state of the user.

U.S. Pat. No. 7,583,253 to Industrial Technology Research Institute discloses a method and apparatus that automatically adjust display parameters according to the visual performance of the user. The apparatus, which includes a display, a detecting system and a control system, automatically adjusts display parameters such as brightness, contrast, font, font size, etc. if visual performance exceeds a threshold value.

U.S. Pat. No. 8,271,865 to Google Inc. discloses a system and method to detect and utilize document reading speed.

U.S. Pat. No. 7,967,731 to Sk Telecom Americas, Inc. discloses a system and method for motivating users to improve their wellness. The system uses complex event processing on sensor and user-interaction data of the users collected over time. The system also uses inference and predictive models and delivers personalized interactions to motivate the users toward their wellness goals.

U.S. Pat. No. 8,083,675 to Dakim Inc. discloses a method and system for providing cognitive stimulation. The user is presented with activities. The activities may change in relation to user's response patterns to create an experience that remains engaging over time.

Commonly assigned co-pending U.S. application Ser. No. 13/274,608, filed on Oct. 17, 2011, entitled "METHOD AND SYSTEM FOR CONDUCTING A HEALTH RISK ASSESSMENT", the entire contents of which are incorporated herein by reference, provides a method and system for conducting a health risk assessment of one or more users, wherein previous responses by multiple users are used to generate specific inquires for a user to provide specific recommended action to the user.

Commonly assigned co-pending U.S. application Ser. No. 13/457,868, filed on Apr. 27, 2012, entitled "SYSTEM AND METHOD FOR ELECTRONIC EVENT CORRELATED MESSAGE DELIVERY", the entire contents of which are incorporated herein by reference, provides a method and system for providing message delivery to one or more users. The method and system, which employ event identification and correlation, are particularly useful in prioritizing messages considered important for the user.

Ways to determine whether a user is engaged during wellness program interaction are desired. Techniques to keep a user engaged during wellness program interaction are also desired.

SUMMARY OF THE INVENTION

The present invention provides a method and system for assessing and enhancing user engagement during wellness program interaction. User engagement includes the user's interest in the wellness program, continued involvement in the wellness program and the user's interest and attention toward the wellness program both before it begins and during the program. In accordance with an embodiment of the invention, human emotion data and/or physiological data are assessed to determine a user's interest in the wellness program interaction. Human emotion data may include facial expression (as determined using, among others, e.g., Facial Action Coding System "FACS" (as derived by Ekman et al., Constants across cultures in the face and emotion, Journal of Personality and Social Psychology, 17(2):124-129 (1971), which discloses that the association between particular facial muscular patterns and emotions is universal)), eye movement or squinting and kinetics, i.e., body language, including, e.g., body posture and gestures (see, e.g., Borg, James, Body Language: 7 Easy Lessons to Master the Silent Language. FT Press, 2010, ISBN 978-0-13-700260-3). Psychophysiological data is created by analysis of psychological data that is an expression of emotion, e.g., analysis of facial expression. Physiological data may include, e.g., skin biophysical properties, heart rate and blood pressure. Physiological data may be collected, e.g., using monitoring devices that are integral with or attached to, e.g., a user's wireless device. See, e.g., FITBIT. The One® wireless trackers (http://www.fitbit.com/home); BodyMedia® FIT system (http://www.bodymedia.com/?utm_source=MSN); and JAWBONE UP band (https://jawbone.com/up). The human emotion data or psychophysiological data or psychophysiological data and/or the physiological data may be employed in conjunction with self-reported questionnaire data to enhance the usability/relevance of the wellness program interaction.

In accordance with an embodiment of the invention, direct inputs and/or indirect inputs are processed to determine a user's interest in the wellness program interaction. Direct inputs, which involve direct interaction between the user and the user's communication device, include, e.g., keystrokes, cursor movement, double tapping to zoom an image, etc. Indirect inputs include, e.g., pause time between direct inputs, keystroke corrections, time on page, time on screen, time in session, whether the user is multitasking, camera images, video images, background noise level, etc. These inputs themselves can be a form of human emotion data or psychophysiological data and/or physiological data. Indirect inputs can also include attributes about the user's connection itself, e.g., the user's Internet Protocol address may provide useful information about the user. Every device connected to the public Internet is assigned a unique number known as an Internet Protocol (IP) address. IP addresses consist of four numbers separated by periods (also called a 'dotted-quad') and look something like 127.0.0.1. Since these numbers are usually assigned to internet service providers within region-based blocks, an IP address can often be used to identify the region or country from which a computer is connecting to the Internet. An IP address may also be used to show the user's general location.

Additional inputs that can used to measure the user's interest or engagement in the wellness program include data from ingestible and implantable sensors; transdermal measurement; galvanic skin responses; brain wave or brain signal measurements, voice/speech recognition; email and message interaction behavior and analysis of natural language.

Even further means for measuring the user's interest or engagement in the wellness program include analysis of the user's consumer purchasing behavior and changes in buying behavior; measuring and analyzing the user's digital social network activity, membership in and use of support groups and membership in and use of community groups and social organizations. The user's buying or purchasing behavior and involvement in social organizations or networks and community activities can also help drive more effective intervention by understanding the user's consumer behavior, social behavior, what motivates the user to take action and their readiness for making change in their lives. Using these direct and indirect inputs the method according the present invention can make inferences about the user's health and/or current willingness or openness to make changes in their life including changes that effect their health and wellness.

In accordance with the invention, a baseline measurement may be taken prior to a wellness program interaction. User data can be taken during a wellness program interaction and compared to the baseline to determine user engagement.

In accordance with an embodiment of the invention, the human emotion data and/or the physiological data and/or the direct inputs and/or the indirect inputs is/are employed to modify the content of the wellness program interaction to try to increase user engagement. Content can include the substance as well as the form/display of the material being provided. Content can also include the modality employed to deliver the material.

The method and system of the invention assist in tailoring the wellness program interaction to the individual user. It is expected that the system and method of the invention will reduce potential development of boredom or frustration by the user. It is also expected that the system and method of the invention will enhance the accuracy of information received by the user. This targeted approach is made possible in part by analysis of human emotion data and/or physiological data and/or direct inputs and/or indirect inputs of the user as compared to previously obtained human emotion data and/or physiological data and/or direct inputs and/or indirect inputs. The collected data can be analyzed to predict which specific interactions will be most effective in keeping the user engaged in the wellness program interaction.

The method of the invention incorporates the following steps to drive effective action by the user: gather human emotion data and/or physiological data and/or direct inputs and/or indirect inputs; compare the gathered data to previously obtained data on human emotion and/or physiology and/or direct inputs and/or indirect inputs to determine user engagement; and modify content of the wellness program interaction if deemed necessary.

The system of the invention may include standard components of an interactive computational device. One component may be an input device such as a keyboard, touch screen, microphone accessing speech recognition software, a camera or a video recorder. A second component may be a data storage device, which may be a hard drive, fixed memory such as a flash drive, laser-based read/write disks or other device capable of accepting, storing, and retrieving electronic information. The data storage device may be in close proximity to the input device, or it may be at a remote location, with access provided by the internet, a telephone link, a wireless link, or other communication channel.

A third component may be a computational device such as a computer or data processor. This component is capable of accessing data from the input device, the data storage device, or other sources, and is able to operate the software modules needed to execute the various aspects of this invention. These software modules, which include various algorithms and rules engines, are also capable of drawing upon databases containing historical data and/or previously obtained user data and comparing current data of the user of the wellness program interaction with this historical data and/or previously obtained user data. Finally, the computational device is able to transfer output data to one or more data storage devices, or directly to an output device. The output device may consist of a video screen, a printer, an audio speaker, a phone or another device capable of providing a communication to the user.

In one embodiment, a desktop or laptop computer may be employed. It may also be a work station or terminal linked to remote data processing and data storage functions. Also, a mobile electronic device, such as a cell phone, a personal digital assistant, or a netbook may be employed. Furthermore, a telephone (either cellular or land line) that is in communication with remote data storage and data processing components may be employed. A device may serve as both the input and the output components.

The invention, as described above, may be based on the interaction of a single user with the wellness program interaction. However, the invention may be similarly based on responses of groups of users, for example a couple or a family unit.

DETAILED DESCRIPTION OF THE PREFERRED EMBODIMENTS

Definitions

Unless defined otherwise, all technical and scientific terms used herein have the same meaning as commonly understood by one of ordinary skill in the art to which the invention belongs. Also, all publications, patent applications, patents, and other references that may be mentioned herein are incorporated by reference in their entirety.

"JavaScript" is a programming language that is often used to create enhanced user interfaces and dynamic websites.

"Real time" as used herein real time is a process, action or transaction that involves updating information without artificial delay, i.e., at the same rate that the information is received.

"Wellness program interaction" includes responding to a HRA questionnaire as well as continued interaction with a wellness program, e.g., receiving wellness program messages, interacting with wellness program tools, and downloading additional wellness program materials.

The present invention relates to a method and system for enhancing user engagement during wellness program interaction. The invention thus includes a component for evaluating the needs of a user in real time and adjusting the wellness program if necessary.

The invention incorporates evaluation of the user and correlating the evaluation with various patterns of user responses. The results of these analyses can be incorporated into rules operating on a rules engine, which is included in software operating on a processing device, such as a mainframe computer, a desktop computer, a laptop computer, or a hand-held computational device such as a personal digital assistant or a cell phone. These rules may be stored in a data storage device, or alternatively, the rules may be generated real time during the wellness program interaction.

The rules generated by this analysis can serve a number of purposes. One purpose is to determine possible actions that will be most effective for the user. Also, the real time analysis of user response, and possible comparison with past associations as contained in the rules engine, may allow the elimination of non-useful or duplicative additional queries/messages to the user. This streamlining of the wellness program interaction and elimination of non-useful queries/messages reduces the time needed to conduct the wellness program interaction, reduces the potential frustration of the user in participating in the wellness program, and improves the overall quality of the output that is provided to the user.

In an additional embodiment, the invention includes enrolling the user in a training regimen to determine a user profile for the user; and using the user profile to predict or determine the actual engagement for the user. The training regimen can include recording and/or associating one or more facial expressions of the user with one or more levels of engagement or evaluating the user's emotional data and/or physiological data and/or direct input and/or indirect input to determine or predict the user's actual engagement.

Another aspect of the invention is the use of data from previous users of the wellness program, or other versions of the wellness program, or from third party sources to determine correlations among various query responses. This information, which comprises a database of responses that is maintained in a form of an electronic data storage device, can be compared to user interaction. These various correlations are used to construct rules that are incorporated within a rules engine operating on a processing device. This processing device receives the responses from a user conducting the wellness program interaction, applies the rules engine derived from past history, and selects the questions/messages that are predicted to be most effective for the user conducting the wellness program interaction. These recommendations are transmitted to an output device, such as a video screen, which is accessible to the user.

According to another embodiment of the invention, user response is used to determine user engagement during wellness program interaction. User response may be used prior to participation of the user in the wellness program interaction, or alternatively may be employed concurrently with the wellness program interaction. The user responses can be compared to previous responses obtained from the user or from a database of other users sometimes known as normative or comparative data. The other user data can be obtained from various sources including other health and wellness programs.

In accordance with the invention, a user's interaction(s) with device(s) is/are used to determine the user's engagement during wellness program interaction. Examples include eye tracking to determine where the user focuses on a page or image, using a web camera to determine facial expressions, using skin sensors to determine muscle reaction, in an effort to gather data on user engagement, which can in turn be used to programmatically alter further system interaction with the user. Program features and content that are most relevant and efficacious can thus be used to enhance the user's experience during the wellness program interaction.

Figure 1:
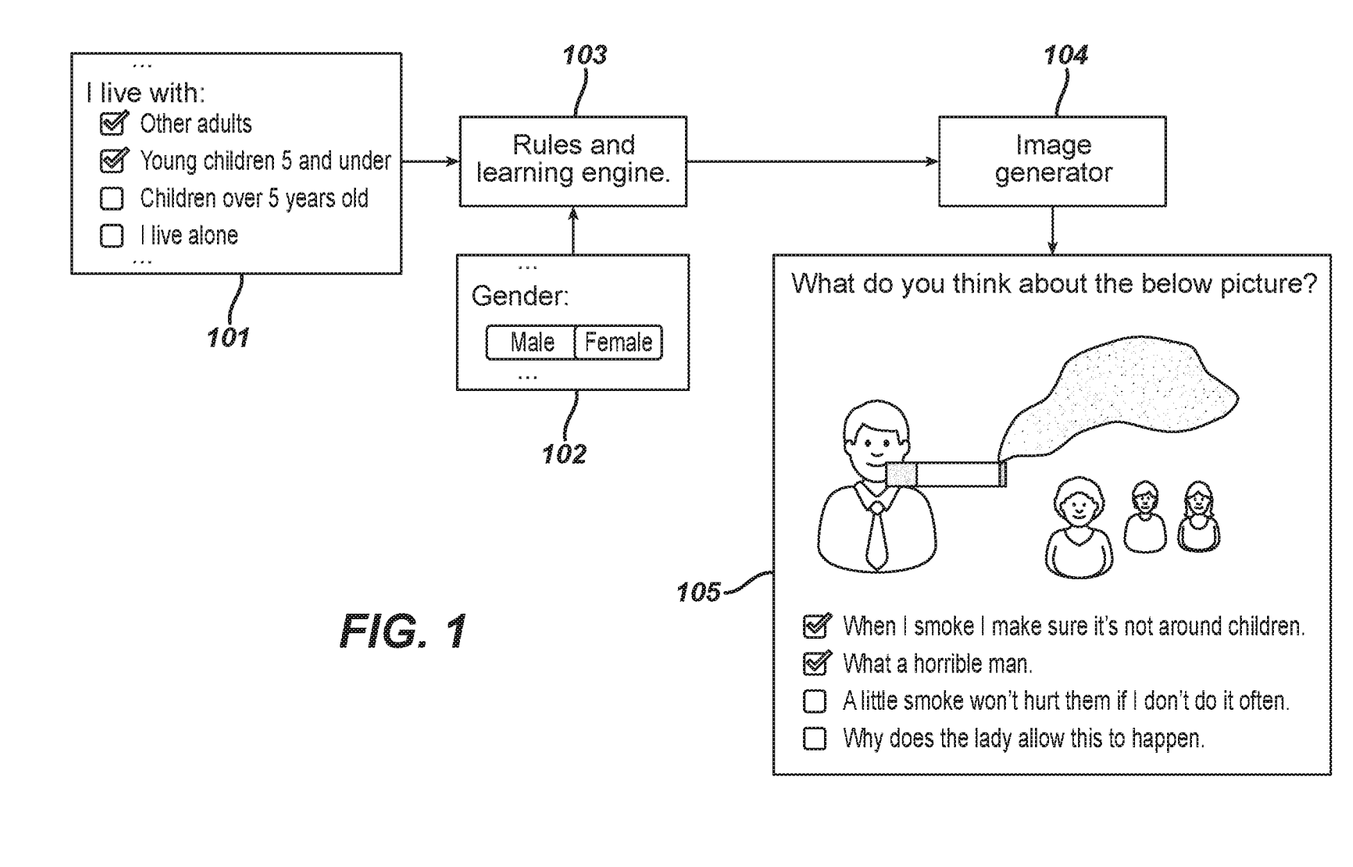
FIG. 1 is a schematic showing a personalized graphic for maintaining user engagement in accordance with an embodiment of the invention.

Referring to FIG. 1, personalized graphics are employed to maintain user engagement. In FIG. 1, user ordinarily a smoker is provided with images of himself/herself or images that resemble himself/herself smoking in front of their spouse and young children. These images personalize the message not to smoke. In accordance with the system and method of the present invention, user provides input such as family information 101 and gender 102. The information is processed by a rules and learning engine 103 which uses an image generator 104 to generate graphics relevant to the user 105. Graphics are often easier to relate to—personalizing them, makes them resonate even more. See, e.g., Ducheneaut et al., Body and Mind, a Study of Avatar Personalization in Three Virtual Worlds, Proc. of CHI (2009), http://www.nickyee.com/pubs/Ducheneaut,%20Wen, %20Yee,%20Wadley %20-%20CHI %202009.pdf. Many can probably relate to the "Mii" characters that are created on the game "Wii Fit" for the Nintendo Wii. Graphic representations can be developed/reshaped over time with new data—much like how it is done with the manually entered data in Wii Fit. See, e.g., http://www.miisearch.com/mii-creator.html?view=miicreator. It is expected that a user looking at images that resemble himself/herself and those close to him/her will be more motivated during wellness program interaction. See, e.g., Can avatars change the way we think and act?, Stanford Report (Feb. 25, 2010). Studies have also shown that humor combined with graphics can motivate people. See, e.g., Puder, The Healthful Effects of Laughter, The International Child and Youth Care Network, Issue 55 (August, 2003), http://www.cyc-net.org/cyc-online/cycol-0803-humour.html. Characters can be used to show a user riding his bike with his daughter, or can show team competitions with team photos moving across a grid in competition to reach the goal first. There could be a check in once a week where team progress can be updated in relation to other teams.

Users can employ a likeness (or a caricature) of themselves and others. After creating the likeness, it can be used as characters in the wellness program interaction. For example, the appearance of a user's face and body can be employed: the user is given a variety of different hairstyles, eye, nose, and mouth shapes, and other features such as facial hair or wrinkles, to select from. Most of the facial features can be further adjusted, including their size, position, color, and alignment. Accessories such as hats and glasses are also available to add, and the height and build of the character can also be adjusted.

Figure 2:
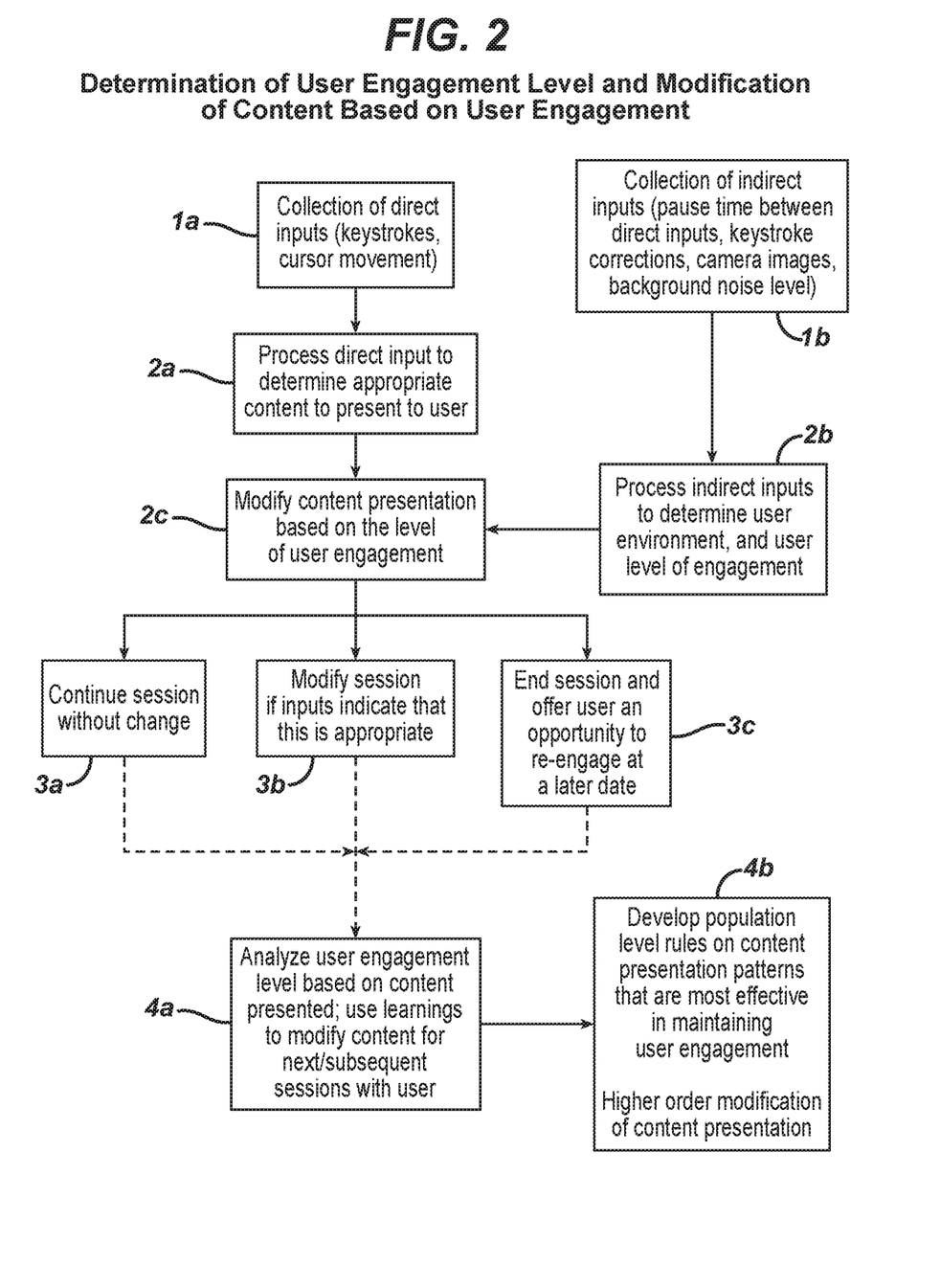
FIG. 2 is a block diagram showing a system for assessing user engagement during wellness program interaction, wherein content may be modified if necessary to maintain user engagement, in accordance with an embodiment of the invention.

Referring now to FIG. 2, a block diagram shows a system and method for assessing user engagement during wellness program interaction. In accordance with the system and method, direct inputs and/or indirect inputs are collected and processed 1*a*, 1*b*. A rules engine operating on a processing device analyzes the inputs in real time 2*a*, 2*b* and modifies content if necessary based on user engagement 2*c*. The system and method thus permit (1) continued wellness program interaction without change 3*a*, (2) continued wellness program interaction with modification in the form of substance and/or form/display to keep the user engaged 3*b* or (3) end of wellness program interaction to offer the user an opportunity to engage at a later date 3*c*. In accordance with an embodiment, user engagement can be analyzed and learnings can be used to modify content during future wellness program interaction 4*a*. In addition, population level rules on content presentation patterns that are most effective in maintaining user engagement can be developed 4*b*.

In accordance with the method depicted in FIG. 2, an output device (not shown) provides wellness program interaction to a user. User interacts with the wellness program interaction via an input device (not shown) that transfers data regarding the interaction to a data storage device (not shown). The output device and the input device may be the same device. A rules engine operating on a processing device (not shown) analyzes the data obtained from data storage device. Based on the operation of the rules engine, the rules engine may modify the interaction with the user.

Figure 3:
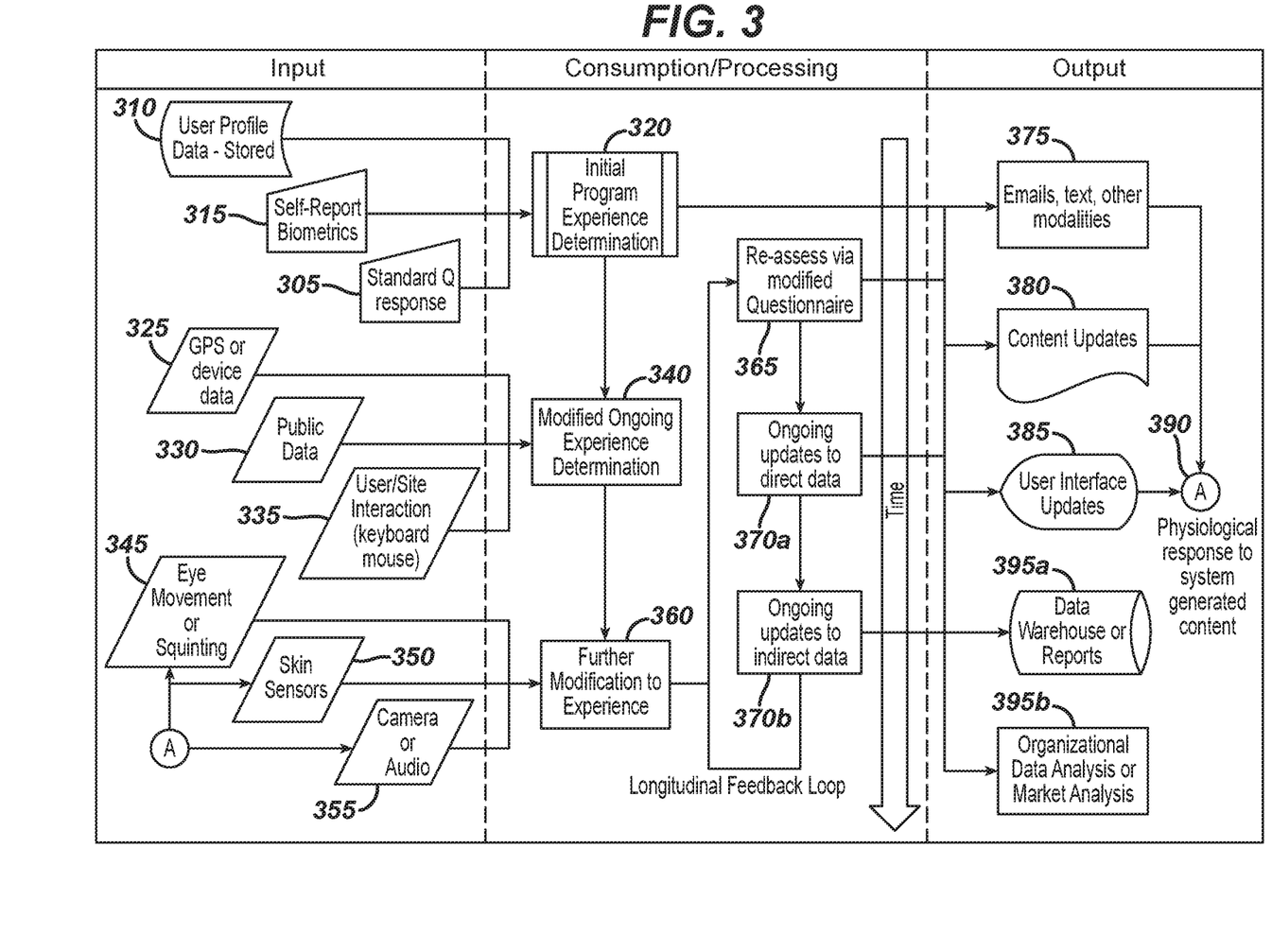
FIG. 3 is a block diagram showing a system for assessing user engagement during wellness program interaction, wherein content may be modified if necessary to maintain user engagement, in accordance with an embodiment of the invention.

Referring now to FIG. 3, a block diagram shows a system and method for assessing user engagement during wellness program interaction similar to that in depicted in FIG. 2.

This involves tailoring images and videos as the user progresses through the wellness program interaction to enhance the user experience. User input can be used to form a more interactive experience, as opposed to a standard wellness program interaction. This approach can provide constant feedback. Instead of using the same questions (i.e. "How does your depression affect your loved ones?"), data can be used to form subsequent questions (e.g., "Sarah, how has your depression affected the limited time you have to spend with Peter?").

Referring to FIG. 3, user responses to queries are collected via an input device 305 and stored in a data storage device 310. This information along with user reported biometric information 315 is gathered and processed to determine an initial program experience 320. At the same time, additional information about the user can be collected. For example, user location can be collected via GPS/pedometer/other biodevice 325, public data that may affect the user, e.g., weather/news can be collected 330, and/or user/device interaction (e.g., web page analysis, mouse behavior, keyboard input and physics) can be collected 335. Depending on the results of the collection of this information, the initial program experience may be modified 340.

At the same time, additional information about the user can be collected, e.g., eye movement or squinting can be collected using, e.g., a camera or a video recorder 345, skin biophysical properties can be collected using skin sensors 350, and facial expression can be collected using, e.g., a camera or a video recorder 355. Depending on the results of the collection of this information, the program experience may be further modified 360.

A modified questionnaire 365 can be employed based on previous user input to reassess the user. Direct data 370*a* and indirect data 370*b* can be continuously monitored and updated.

The wellness program can interact with the user via e-mails, texts or other modalities 375; content can be updated 380; and user interface can be updated 385, and all three can be employed to determine physiological response to content 390.

In addition, all of the above-mentioned data can be collected and stored in a data warehouse or report 395*a* and analyzed at a higher level. For example, user information, in the form of questionnaire profile, inputs, etc. can be added to a data set organizationally, across market segment, etc. and fed back into the system when needed 395*b*

Based on the operation of the rules engine, the rules engine may (1) select additional queries/messages for the user, and/or (2) change the form/display of the queries/messages. User responds to these additional queries/messages and/or form/display via an input device (not shown) to a data storage device (not shown). The stored data from data storage device is accessed by rules engine operating on processing device (not shown) to predict one or more actions most likely to help the user be more engaged. This additional input to the rules engine permits greater ability to tailor the (1) queries/messages; and/or (2) form/display provided to the user, and increases the likelihood of the user achieving success in improving health and attaining his/her personal objectives. These queries/messages and/or form/display are transferred to an output device, which communicates the queries/messages and/or form/display to the user.

Figure 4:
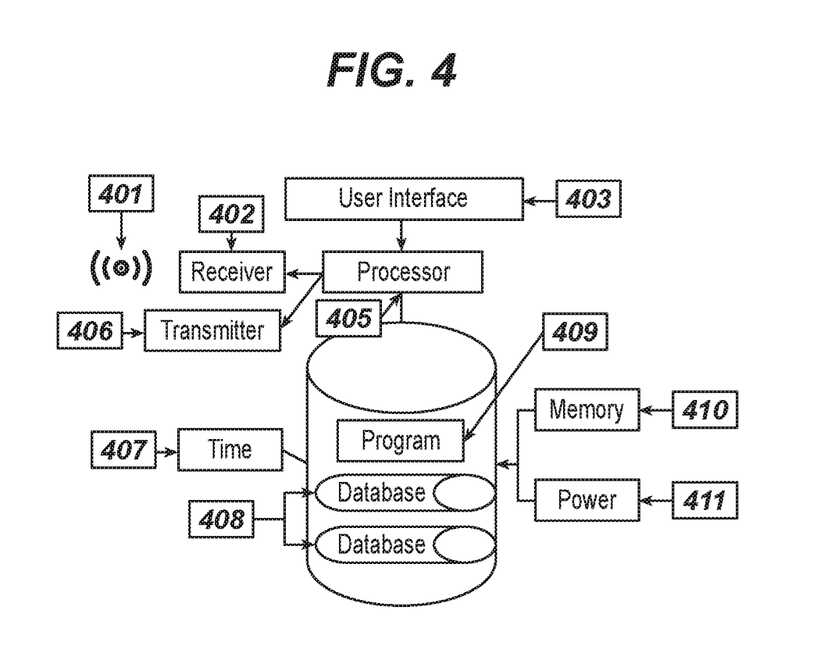
FIG. 4 is a schematic that illustrates a server that may be employed when using the method and system of the present invention.

FIG. 4 is a schematic that illustrates a server that may be employed when using the method and system of the present invention. Referring to FIG. 4, the server can contain different means of receiving human emotion data and/or physiological data and/or direct inputs and/or indirect inputs 401. For example, input device such as a keyboard, touch screen, microphone accessing speech recognition software, a camera or a video recorder, etc. A receiver 402 can be used to allow the processor 405 to cause the data to be stored in specific databases 408 in uniform format and time. The data can then be used by a program 409 executable to perform the functions as described above by means of a series of algorithms. The server can additionally include a user interface 403, a processor for the software 405, a means of power 411, memory 410, and a means of keeping real time 407 in relation to the specific location of the individual (e.g., connecting the user's cell phone to the system to change time accordingly when required due to the user traveling.) A transmitter 406 in logical communication with the processor 405 transmits one or more messages to one or more network access devices associated with the user (not shown).

Figure 5:
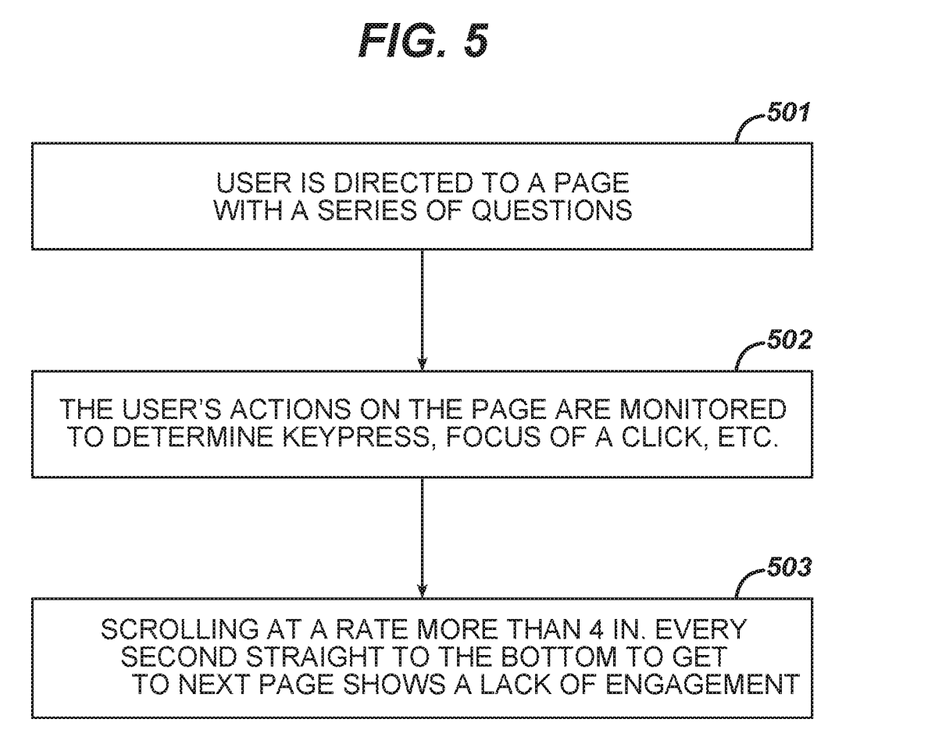
FIG. 5 is a block diagram showing the use of reading speed and content assimilation in accordance with an embodiment of the invention.

FIG. 5 is a block diagram showing reading speed and content assimilation. Referring to FIG. 5, the user is directed to a page with a series of questions 501 and the user's actions on the page are monitored 502 using, e.g., JavaScript. For example, JavaScript can be employed to determine keypress, focus of a click, etc. This allows the system according to an embodiment of the invention to determine lack of user engagement if the scrolling of the pages is too fast, e.g. 4 inches every second 503.

Figure 6A:
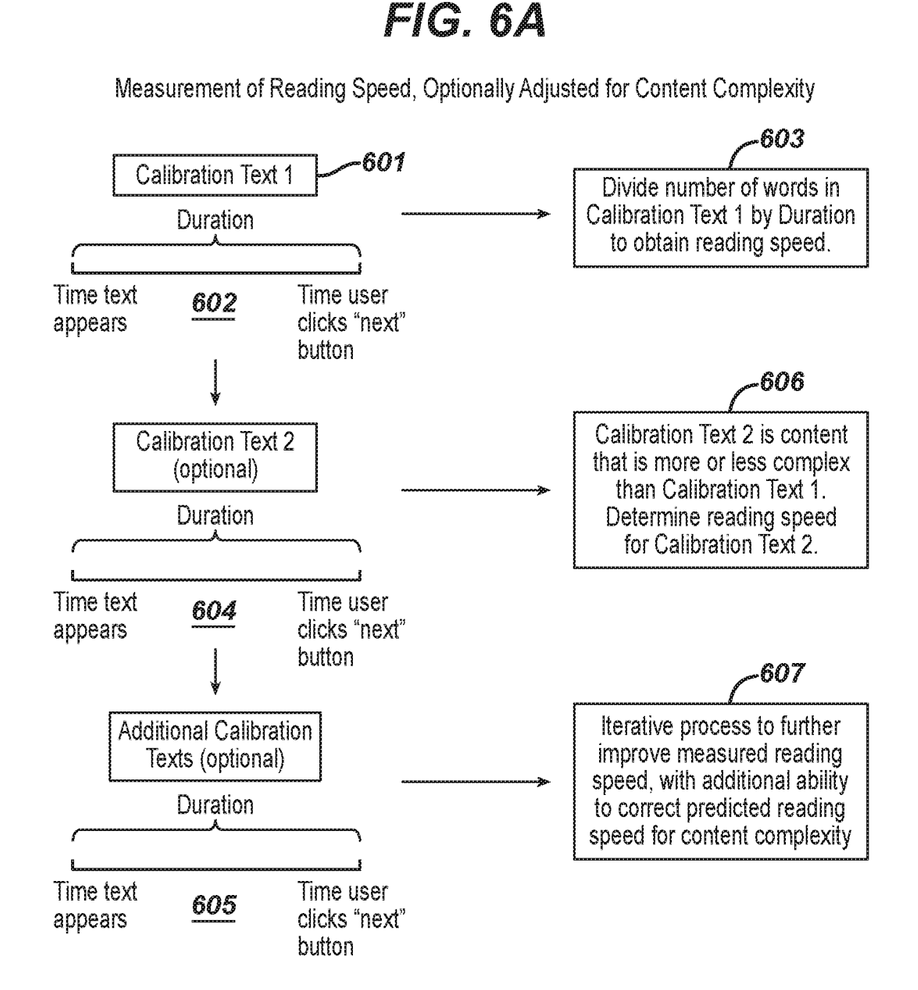
FIGS. 6A and 6B are schematics showing the use of reading speed and content assimilation in accordance with an embodiment of the invention.
Figure 6B:
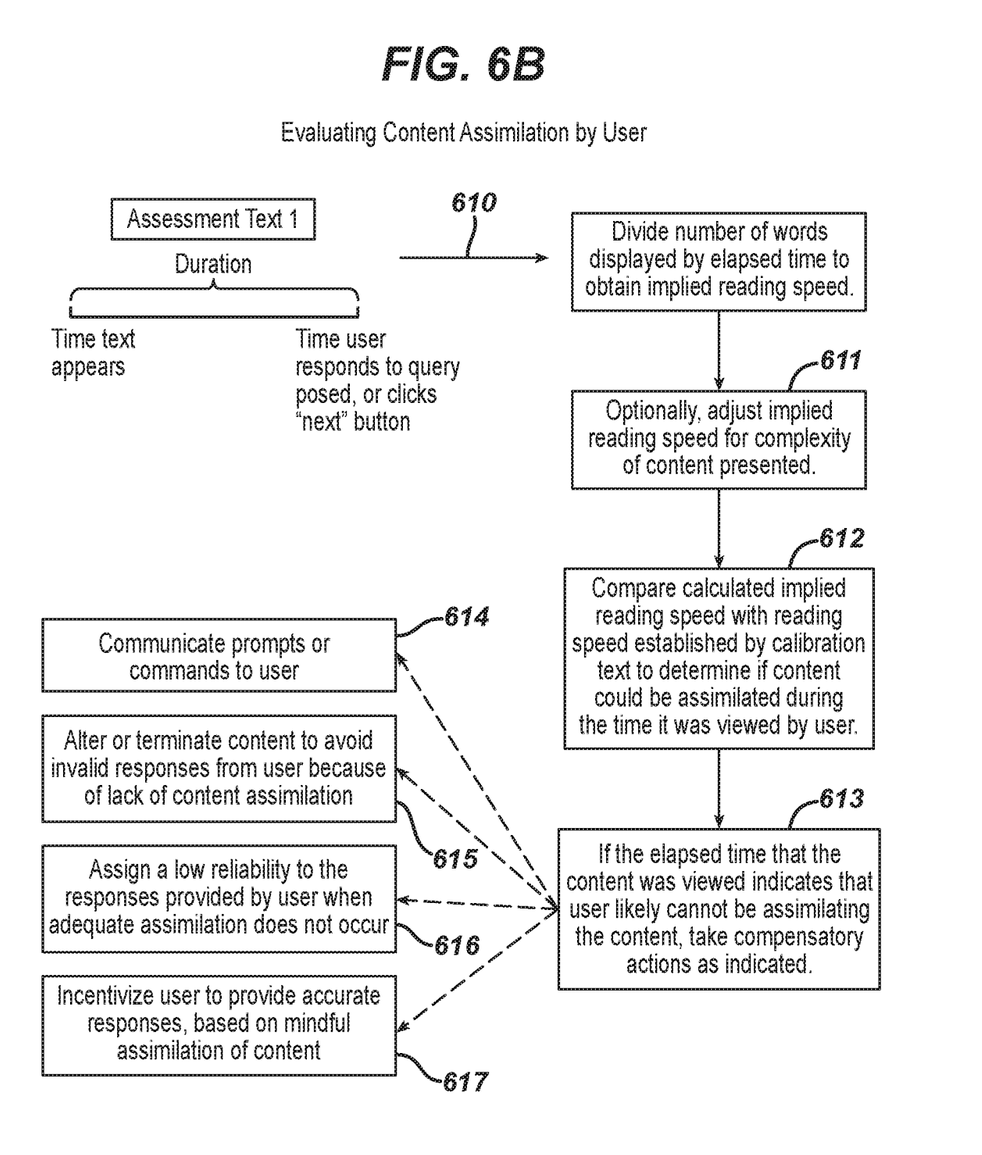

FIGS. 6A and 6B are schematics showing reading speed and content assimilation. Referring to FIG. 6A, reading speed is measured and optionally adjusted for content complexity. User is directed to a page to assess baseline reading speed. An entry, "Calibration Text 1", appears on the page and user reads the entry 601. The duration of time from when the entry appeared on the page to the time when the user clicks "next" button is determined 602. Reading speed is determined by dividing the number of words in Calibration Text 1 by the duration of time 603. The same steps may be repeated for "Calibration Text 2" 604, "Calibration Text 3" 605 and so on. The Calibration Text used in the repeated steps can be more or less complex than the previous text 606. Using an iterative process will improve measured reading speed. Predicted speed can be corrected for content complexity 607.

Referring to FIG. 6B, content assimilation by the user is evaluated by comparing the implied reading speed with the reading speed established using the calibration text to determine if the content could be assimilated during the time it was viewed by the user. An Assessment Text 1 is evaluated in the same manner as the Calibration Text 610 by dividing the number of words by the duration of time. Optionally, the reading speed is adjusted for content complexity 611. The calculated implied reading speed is then compared to the speed established by the Calibration Text 612. If the elapsed time that the content was viewed indicates that the user likely cannot be assimilating the content 613, the content can be modified to (1) communicate prompts or commands to the user 614; (2) alter or terminate the content to avoid invalid responses from the user because of lack of content assimilation 615; (3) assign a low reliability to the responses provided by the user when adequate assimilation does not occur 616; and/or (4) incentivize the user to provide accurate responses based on mindful content assimilation 617.

Figure 7:
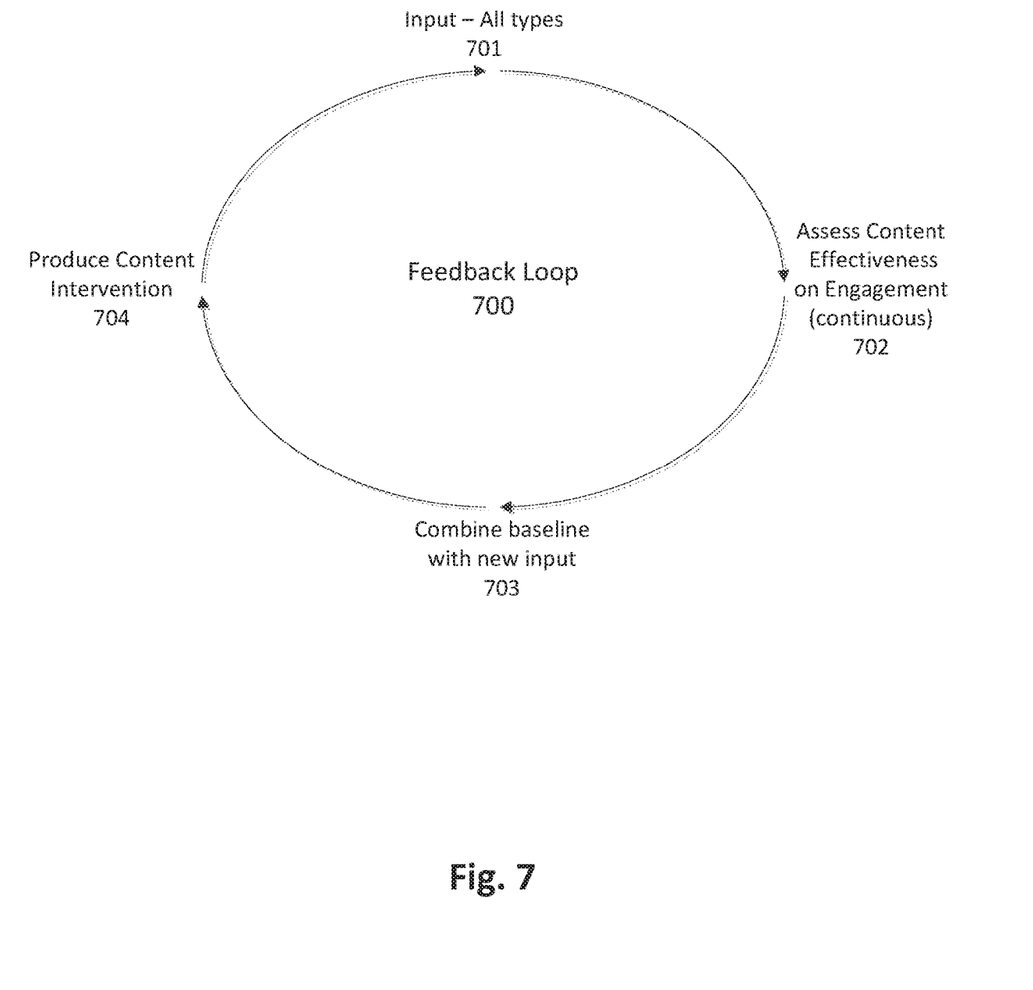
FIG. 7 is a diagram showing a feedback loop of the assessment of user engagement based on inputs and modifying the content in accordance with an embodiment of the invention.

FIG. 7. is a diagram showing a feedback loop 700 according to an embodiment of the invention. Referring to FIG. 7, input 701, which can be any type, is collected from the user of the wellness program. The program content is assessed to measure its effectiveness on the engagement of the user 702. The input collected is combined and compared to new input 703 and the content is modified, if needed, to improve engagement 704. The method of assessing engagement and then modifying the content to improve engagement can be done with one cycle of the feedback loop, if only one content intervention is needed to produce sufficient engagement, more than one cycle or continuously if needed to achieve sufficient engagement of the user during the wellness program interaction.

The foregoing examples are not intended to limit the scope of the present invention, which may be set out in the claims. In particular, various equivalents and substitutions will be recognized by those skilled in the art in view of the foregoing disclosure and these are contemplated to be within the scope of the invention.

What is claimed:

1. At a computerized system including a display device, at least one processor, a memory, an output device and a wellness program application stored in the memory, a computer implemented method for enhancing user engagement during the use of the wellness program, the method comprising the steps of:
    a. collecting human emotion data and/or physiological data and/or direct inputs and/or indirect inputs to establish a user baseline measurement;
    b. presenting the user with wellness program content information including health related content information;
    c. collecting at least two sets of data from the user elected from emotional data; physiological data; direct inputs and indirect inputs for comparison with the human emotion data and/or physiological data and/or direct inputs and/or indirect inputs obtained in step a.;
    d. executing a first rules engine containing rules, wherein the first rules engine analyzes in real time the at least two sets of data selected from emotional data; physiological data; direct inputs and indirect inputs from step c. and compares such data with the human emotion data and/or physiological data and/or direct inputs and/or indirect inputs obtained in step a for determining a user's interest in the wellness program interaction such that the first rules engine, based on the at least two sets of data selected from emotional data; physiological data; direct inputs and indirect inputs, modifies the wellness program content information; and
    e. providing the modified content information to the user via the output device to enhance user interest in the wellness program, continued involvement in the wellness program and the user's interest and attention toward the wellness program.

2. The method of claim 1, further comprising capturing an image of the user with a camera connected to the system, and wherein the processor analyzes the image to determine a level of user interest in the wellness program, continued involvement in the wellness program and the user's interest and attention toward the wellness program content information, including health related content.

3. The method of claim 2, further comprising analyzing one or more psychophysiological responses of the user.

4. The method of claim 3, wherein the one or more psychophysiological responses is a facial expression, and wherein whether a brow is furrowed is determined to indicate an angry mood, an upset mood, or an intensity of a mood, whether the brow is unfurrowed is determined to indicate a neutral mood, a content mood, or a mood of lesser intensity, and a user's mouth features are analyzed to determine if the user is smiling, frowning, angry, experiencing an intense mood, or experiencing a neutral mood.

5. The method of claim 3, wherein the one or more psychophysiological responses is a facial expression, and wherein analyzing the facial expression includes identifying a change in a location of a facial feature, and using the change in the location to determine user interest in the wellness program, continued involvement in the wellness program and the user's interest and attention toward the wellness program content information.

6. The method of claim 5, wherein analyzing the change in the location of the facial feature includes determining that a brow, a wrinkle, a dimple, a hairline, an ear, a nose, a mouth, or a chin is located in a different location.

7. The method of claim 2, wherein analyzing the image to determine user interest in the wellness program, continued involvement in the wellness program and the user's interest and attention toward the wellness program content information includes: comparing current information related to a current image with previous information related to a previous image; identifying a differential describing how the current information differs from the previous information; and using the differential to determine user engagement.

8. The method of claim 2, wherein analyzing the image to determine user engagement includes identifying a level of user movement, and using the user movement to determine user interest in the wellness program, continued involvement in the wellness program and the user's interest and attention toward the wellness program content information.

9. The method of claim 2 further comprising: determining that the modified content information did not provide the desired user interest in the wellness program, continued involvement in the wellness program and the user's interest and attention toward the wellness program content information, and adjusting the modified content information to increase user engagement.

10. The method of system of claim 1, further comprising: enrolling the user in a training regimen to determine a user profile for the user; and using the user profile to determine the actual user interest in the wellness program, continued involvement in the wellness program and the user's interest and attention toward the wellness program content information.

11. The method of claim 10, wherein enrolling the user in the training regimen includes associating one or more facial expressions of the user with one or more levels of user interest in the wellness program, continued involvement in the wellness program and the user's interest and attention toward the wellness program content information.

12. The method of claim 1, wherein physiological data of the user is determined during the wellness program.

13. The method of claim 12, wherein the physiological parameters are selected from the group consisting of skin biophysical measures, heart rate, blood pressure and temperature.

14. The method of claim 1, wherein the direct input is capturing an image of the user and analyzing the image to determine a level of user interest in the wellness program, continued involvement in the wellness program and the user's interest and attention toward the wellness program content information.

15. The method of claim 14, wherein the captured image is a facial expression, and wherein whether a brow is furrowed is determined to indicate an angry mood, an upset mood, or an intensity of a mood, whether the brow is unfurrowed is determined to indicate a neutral mood, a content mood, or a mood of lesser intensity, and a user's mouth features are analyzed to determine if the user is smiling, frowning, angry, experiencing an intense mood, or experiencing a neutral mood.

16. The method of claim 1, wherein the physiological data is selected from the group consisting of skin biophysical measures, heart rate, blood pressure and temperature.

17. The method of claim 1, wherein the steps are performed sequentially.

18. The method of claim 1, wherein the steps are repeated at least two times.

* * * * *